United States Patent [19]

Retallick, III

[11] Patent Number: 5,988,162
[45] Date of Patent: Nov. 23, 1999

[54] APPARATUS AND METHOD FOR TREATING THE LUNGS

[76] Inventor: Donald L. Retallick, III, 4227-B, Arnold Ave., P.O. Box 8207, Naples, Fla. 33941-8207

[21] Appl. No.: 08/556,099

[22] Filed: Nov. 9, 1995

[51] Int. Cl.⁶ .................................................. A61M 16/00
[52] U.S. Cl. ............................... 128/203.12; 128/200.14; 128/200.19; 128/203.28
[58] Field of Search ......................... 128/200.11, 200.14, 128/200.19, 200.21, 203.12, 205.13, 912, 202.28, 202.29, 203.11, 200.23, 200.18, 203.28, 200.29, 204.28

[56] References Cited

U.S. PATENT DOCUMENTS

| | | | |
|---|---|---|---|
| 3,502,077 | 3/1970 | Joseph | 128/200.14 |
| 3,769,973 | 11/1973 | Esbenshade, Jr. | 128/200.14 |
| 4,253,468 | 3/1981 | Lehmbeck | 128/200.18 |
| 4,446,864 | 5/1984 | Watson et al. | 128/202.28 |
| 4,676,239 | 6/1987 | Humphrey | 128/203.28 |
| 4,796,615 | 1/1989 | Bullock et al. | 128/202.27 |
| 4,953,547 | 9/1990 | Poole, Jr. | 128/203.12 |
| 5,072,726 | 12/1991 | Mazloomdoost et al. | 128/200.14 |
| 5,099,833 | 3/1992 | Michaels | 128/200.14 |
| 5,181,508 | 1/1993 | Pool, Jr. | 128/203.12 |

FOREIGN PATENT DOCUMENTS 9300952  1/1993  WIPO .

*Primary Examiner*—John G. Weiss
*Assistant Examiner*—V. Srivastava

[57] ABSTRACT

Apparatus and method for the simultaneous administration of pressurized oxygen, a nebulized mist of bronchodilator, and an additional liquid medicant into the trachea and lungs of a patient exhibiting little or no respitory function. The oxygen is fed through a tube from a manually operable resuscitator such as an Ambu-Bag. The nebulized bronchodilator is fed from a conventional nebulizer into the tube carrying oxygen from the resuscitator. The additional liquid medicant is fed from the needle of a pre-filled syringe containing the liquid medicant directly into the tube carrying pressurized oxygen and the mist of nebulized bronchodilator. The tube carrying the oxygen, the bronchodilator and the additional liquid medicant is connected to the upper end of an endotracheal tube which terminates in the patient's trachea.

3 Claims, 1 Drawing Sheet

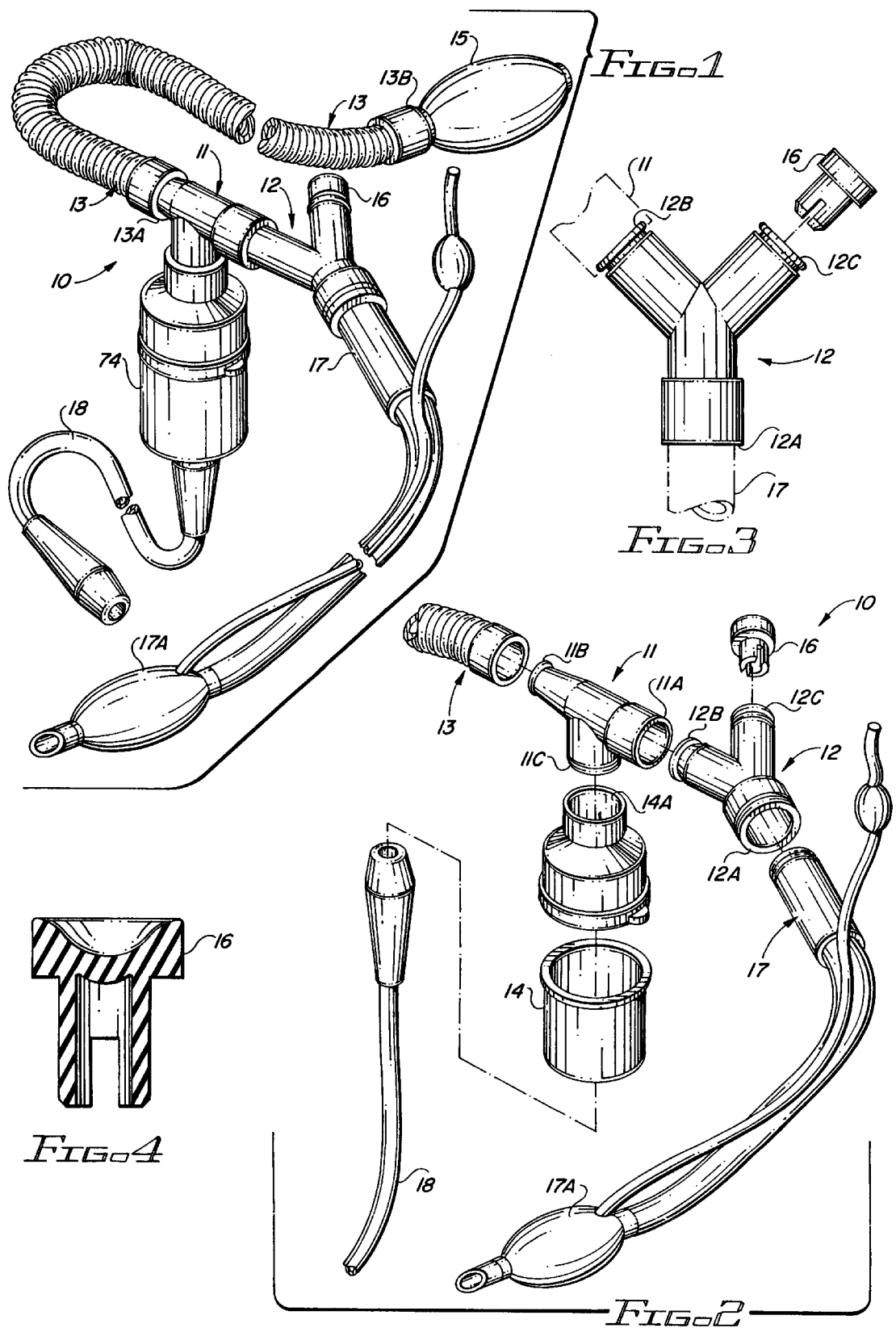

APPARATUS AND METHOD FOR TREATING THE LUNGS

FIELD OF INVENTION

My invention lies in the field of medical apparatus for treating the lungs and trachea of a patient who has difficulty breathing or has stopped breathing. More particularly, my invention permits the simultaneous administration of oxygen, a nebulized bronchodilator, and an additional medicant such as lidocaine to a patient with low or no respitory function.

BACKGROUND OF THE INVENTION

The administration of oxygen into the lungs has long been used for the treatment of low respiratory function resulting from such conditions as asthma, croup, pneumonia, mucus accumulation, pulmonary edema, congestive heart failure and coronary thrombosis. In practice, the oxygen under pressure was fed to the upper end of an endotracheal tube extending from the patient's mouth down into the trachea.

More recently, it has been found helpful to introduce various medicants into the trachea and the lungs through the endotracheal tube to moisten tissue, thin accumulated mucus or otherwise stabilize the patient despite the danger of interrupting the administration of oxygen while one or more medicants was moved down the endotracheal tube and into the trachea and lungs.

Thus there was a need for apparatus that would permit the simultaneous administration of oxygen and one or more medicants into the lungs of a patient with little or no respitory function.

This need was particularly acute in emergency situations such as in ambulances transporting a patient who exhibits low respitory function. Emergency personnel are trained to insert an endotracheal tube connected to an Ambu-Bag which when manually manipulated forces oxygen down the endotracheal tube into the lungs. But, for example, if the emergency personnel realize breathing is impeded by an accumulation of mucus, they have the life threatening choice of interrupting the flow of oxygen in order to inject a medicant capable of breaking up the mucus in the lungs.

SUMMARY OF THE INVENTION

My invention was born as the result of the death of a patient with very low respitory function being administered oxygen from an Ambu-Bag in an ambulance on its way to a hospital. Knowing the patient's dangerously deteriorating breathing resulted from acute bronchial constriction, the Ambu-Bag was disconnected and epinephrine injected down the endotracheal tube into the lungs. There was no way to feed nebulized epinephrine to the lungs and by the time the epinephrine had been injected and the Ambu-Bag reconnected to the endotracheal tube, the patient had expired.

Using components available at most medical supply houses, I constructed a prototype of my apparatus which can be used by trained emergency medical personnel such as ambulance attendants as well as by nurses and hospital technicians to simultaneously administer oxygen, a nebulized bronchodilator and an additional medicant directly into the lung area of a patient with little or no respitory function.

Briefly stated, my apparatus consists of seven components which are joined together in a particular way. The components preferably made of synthetic materials such as polyvinyl chloride, nylon and neoprene are (1) a T-shaped tube having two open upper ends and a lower open end, (2) a Y-shaped tube having two open rear ends and a front open end, (3) a self-sealing plug, (4) a flexible tube having two open ends, (5) a nebulizer having an upper discharge port, (6) a resuscitator such as an Ambu-Bag, and (7) an endotracheal tube.

Assembly of my apparatus is accomplished by connecting the upper discharge port of the nebulizer to the lower end of the T-shaped tube. One of the upper ends of the T-shaped tube is connected to one end of the flexible tube whose other end is connected to the manually operated resuscitator. The other upper end of the T-shaped tube is connected to one of the rear ends of the Y-shaped tube whose front end is connected to the upper end of the endotracheal tube. The other rear end of the Y-shaped tube is closed by the self-sealing plug which permits penetration by the needle of a syringe filled with a liquid medicant to inject the medicant into the stream of oxygen and nebulized bronchodilator being delivered to the lungs.

Preferably the assembled apparatus is stored, for example, in an emergency vehicle or ambulance, with its resuscitator and the endotracheal tube removed and separately stored near by. Then when, for example, a patient is loaded onto an ambulance in need of oxygen, the emergency personnel will insert the endotracheal tube down the patient's throat into the trachea. The unique apparatus of my invention is connected to the endotracheal tube and to the Ambu-Bag whereby oxygen can be promptly administered preferably along with a nebulized bronchodilator such as epinephrine or isoetharine.

However, should the patient's condition require an additional medication such as lidocaine to prevent cardiac arrhythmia or naloxone to prevent or reverse an alcohol or drug induced coma, the needle of a pre-filled syringe containing the desired medication can be inserted through the self-sealing plug in the Y-shaped tube to inject the medicant into the stream of pressurized oxygen and nebulized bronchodilator so that the additional medication is fed to the patients lungs simultaneously with oxygen and the nebulized bronchodilator.

BRIEF DESCRIPTION OF THE DRAWINGS

FIG. 1 is a perspective view of a preferred form of my apparatus for simultaneously administering oxygen, a nebulized bronchodilator and an additional medicant to the trachea and lungs.

FIG. 2 is an exploded view of the major components used in the assembly of a preferred embodiment of my apparatus.

FIG. 3 is a detailed view of the Y-shaped tube and the self-sealing plug used in my apparatus.

FIG. 4 is a cross-sectional view of the self-sealing plug.

DETAILED DESCRIPTION OF THE PREFERRED EMBODIMENT

Referring to the attached drawings, FIG. 1 shows apparatus 10 for simultaneously administering oxygen and medicants to the lungs of a patient with little or no respitory function.

Apparatus 10 includes T-shaped tube 11 having two open upper ends 11A and 11B and a lower open end 11C and a Y-shaped tube 12 having a front open end 12A and two rear open ends 12B and 12C. Tubes 11 and 12 are preferably molded from polyvinyl chloride resin. Apparatus 10 also includes a flexible tube 13 with two open ends 13A and 13B preferably made of nylon and about 10 inches in length, all as best shown in FIG. 2.

Apparatus 10 also includes four components well known to the medical community, namely, a nebulizer 14 having an upper discharge port 14A, a manually operated resuscitator 15 often called an Ambu-Bag, a neoprene self-sealing plug 16 similar to the plug used in the VACUTAINER™ made by Becton Dickinson, and finally an endotracheal tube 17 which may or may not include an air-activated cuff 17A to secure the endotracheal tube within the trachea.

As previously explained, the foregoing components are assembled and used in a particular way. The upper discharge port 14A of the nebulizer is connected to the lower open end 11C of T-shaped tube 11. As shown in FIGS. 1 and 2, nebulizer 14 is connected to tube 18 supplying pressurized air and the nebulizer filled with a bronchodilator such as epinephrine or isoetharine.

One end 13A of flexible tube 13 is connected to one upper end 11B of T-shaped tube 11 and its other end 11A is connected to one rear end 12B of Y-shaped tube 12 whose front end 12A is connected to the upper end of endotracheal tube 17 as best shown in FIG. 2. Rear end 12C of tube 12 is plugged by the self-sealing plug 16 best shown in FIGS. 3 and 4.

The resuscitator 15 is connected to the other end 13B of flexible tube 13 to supply pressurized oxygen to the lungs. When my apparatus is used in a hospital, the resuscitator would likely be the hospital's respirator. However, in an emergency situation, resuscitator 15 would likely be a well known manually operated Ambu-Bag as shown in FIG. 1.

In most ambulance transported situations in which a patient is in need of support to continue breathing, my apparatus would be used to administer to the lungs both oxygen from an Ambu-Bag 15 and a nebulized bronchodilator from nebulizer 14. However, if the patient's condition requires an additional medicant, the self-sealing plug 16 is pierced by the needle of a pre-filled syringe (not shown) containing the desired medicant in order to inject the liquid medicant directly into the stream of pressurized oxygen and nebulized bronchodilator to be carried by the pressurized stream into the lungs of the patient to support his fight for life.

Regardless of whether oxygen and nebulized bronchodilator alone or oxygen, bronchodilator and an additional medicant are fed simultaneously to the trachea and lungs, it is the flow of oxygen under pressure from the Ambu-Bag or more sophisticated resuscitator 15 which directs the nebulized bronchodilator and the other medicant down the endotracheal tube and into the lungs of the patient.

While I have shown and described a preferred embodiment of my invention it will be apparent that various changes and structural modifications may be made without departing from the scope and spirit of my invention. The scope of my invention is defined only by the appended claims.

I claim:

1. A light weight emergency apparatus for simultaneously introducing oxygen, a nebulized bronchodilator and a liquid medication through an endotrachael tube into the lungs of a patient comprising a T-shaped tube having two open upper ends and a lower open end, a Y-shaped tube having two open rear ends and a front open end, a self-sealing plug, a flexible tube having two open ends, a nebulizer having an upper discharge port, a manually operated resuscitator, and an endotrachael tube, wherein the upper discharge port of the nebulizer is connected to the lower end of the T-shaped tube, one end of the flexible tube is connected to one upper end of the T-shaped tube and the manually operated resuscitator is connected to the opposite end of the flexible tube, one of the rear ends of the Y-shaped tube is connected to the other upper end of the T-shaped tube, the self-sealing plug is inserted into the other rear end of the Y-shaped tube, and the endotrachael tube is connected to the front end of the Y-shaped tube, thereby permitting insertion of the endotrachael tube into the patient's trachea so oxygen from the resuscitator, a nebulized bronchodilator from the nebulizer and a liquid medication injected through the self-sealing plug in the Y-shaped tube are introduced simultaneously into the patient's lunges.

2. Apparatus as set forth in claim 1 in which the T-shaped tube and the Y-shaped tube are molded from a polyvinyl chloride resin, the self-sealing plug is made of neoprene, and the flexible tube is made of nylon.

3. A method for simultaneously administering to the trachea and lungs of a patient a pressurized stream of oxygen, a nebulized mist of bronchodilator, and a separate liquid medicant in which the oxygen is supplied by a tube from a manually operated resuscitator, the nebulized mist of bronchodilator is fed from a nebulizer into the stream of oxygen, and the separate liquid medicant is injected from the needle of a pre-filled syringe in liquid form directly into the stream of oxygen and nebulized mist of bronchodilator and the oxygen, the mist of bronchodilator and the separate liquid medicant are fed from the tube into the patient's trachea through an endotrachael tube terminating in the patient's trachea.

* * * * *